United States Patent [19]

Singh et al.

[11] Patent Number: 5,215,743
[45] Date of Patent: Jun. 1, 1993

[54] TUMOR NECROSIS FACTOR FORMULATIONS

[76] Inventors: Maninder Singh, 1222 Donald Dr., Rodeo, Calif. 94572; Flint Smith, 479 Crescent St., #31, Oakland, Calif. 94610

[21] Appl. No.: 181,077

[22] Filed: Apr. 13, 1988

[51] Int. Cl.⁵ .................... A61K 45/05; A61K 37/02
[52] U.S. Cl. .................................. 424/85.1; 514/8; 514/21; 514/777; 514/970
[58] Field of Search ............... 424/85.1; 514/8, 21, 514/777, 970

[56] References Cited

U.S. PATENT DOCUMENTS

| | | |
|---|---|---|
| 4,447,355 | 5/1984 | Sakamoto et al. .............. 424/101 |
| 4,457,916 | 7/1984 | Hayashi et al. ................. 424/101 |
| 4,650,674 | 3/1987 | Aggarwal et al. ............... 424/85.1 |
| 4,677,063 | 6/1987 | Mark et al. ..................... 424/85.1 |
| 4,677,064 | 6/1987 | Mark et al. ..................... 424/85.1 |
| 4,762,857 | 8/1988 | Bollin, Jr. et al. .............. 514/777 |
| 4,797,388 | 1/1989 | Francis .......................... 514/23 |
| 4,810,827 | 3/1989 | Mitsuhashi et al. ............. 514/53 |

*Primary Examiner*—Jacqueline Stone

[57] ABSTRACT

Compositions are described that are suitable for formulating cytokines, preferably tumor necrosis factor, that maintain their biological activities over a wide range of temperatures by, among other aspects, decreasing them sensitivity to agitation, and preventing oligomer and particulate matter formation.

13 Claims, 5 Drawing Sheets

TUMOR NECROSIS FACTOR FORMULATIONS

TECHNICAL FIELD

This invention relates generally to the field of immunology, and more particularly to the formulation of cytokines that are pharmaceutically acceptable for administration to patients. More specifically, it relates to pharmaceutical formulations of tumor necrosis factor for parenteral administration.

BACKGROUND ART

Tumor necrosis factor (TNF) is a protein having a molecular weight of about 39,000. It has been cloned from a number of species, and has been expressed in several expression systems. Additionally, muteins of recombinant TNF have been constructed which lack amino acids from the N-terminus of the molecule, or which lack, or have greatly reduced cysteine content. The biological effects of TNF were first described by Carswel et al., (PNAS (U.S.A.) (1975) 72:3666) as a factor present in serum that was induced by endotoxin, and which caused necrosis of certain types of tumors. More recently, recombinantly produced human TNF has also been shown to be an effective anti-cancer agent (Pannica et al., (Nature (London) (1984) 312:724–729), Shirai et al., (Nature (London) (1985) 313:803), Wang et al., (Science (1985), 228:149). TNF has also been reported to inhibit a variety of bacterial or viral infections, either alone or in combination with other lymphokines or cytokines.

Other activities ascribable to TNF include activation of polymorphonuclear leukocytes (Shalaby et al. Journal of Immunology (1985), 135:2069), stimulation of bone resorption and inhibition of bone formation (Bertolini et al., Nature, 319:516), inhibition of lipoprotein lipase (Beutler et al., Nature, 316:552 (1985)), and stimulation of collagenase and prostaglandin $E_2$ production, (Dayer et al., Journal Experimental Medicine, 162:2163 (1985)). TNF is also thought to stimulate fibroblast growth, (Sugarman et al., Science, 230:943 (1985)) and induce interleukin-1, (Nawroth et al., Journal Experimental Medicine, 163:1363 (1986)).

Despite the enormous clinical potential of TNF, suitable prophylactic or therapeutic formulations of the molecule have not been described. In this regard, it is desirable to have formulations that stabilize or maintain the biological activity of TNF, as well as prevent or retard the formation of aggregates, or oligomers, of TNF. The two phenomena are generally unrelated in that biological activity may be independent of, and not affected by aggregation. Aggregated biomolecules, however, are known to have the undesirable property of increased immunogenicity. Bach, J-F. Immunologic Tolerance in Immunology Immunology 2nd ed. chap. 20., pages 575–590 (Ed J-F Bach, R. S. Schmartz, 1982).

Additionally, it is further desirable to develop TNF formulations that are free of particulate matter, as visual clarity in the clinical setting is often considered by the physican as confirmation that the formulation meets U.S.P criteria. Formulations administered by injection should be free of visible particulate matter such that they should not contain more than 1000 or 10,000 particles having sizes of 25 $\mu$m and 10 $\mu$m, respectively. Moreover, for obvious economic reasons, it is particularly important to develop a formulation that is free of particulate matter for the shelf life of the formulation.

Lastly, it is apparent that it is desirable to have formulations that are relatively temperature insensitive, and display all the properties described above over a significant temperature range.

Formulations that stabilize TNF activity are shown in European Patent Application 83301740.3, inventors Sakamoto et al., and in European Patent Application 85106915.3, inventors Sakamoto et al. The former shows a method for stabilizing TNF, either in solution or in solid form using a combination of albumin, gelatin, globulins, protamines, and a salt thereof. It is important to note that while the activity of TNF is enhanced, this method does not reduce TNF oligomer formation. European Patent Application 85106915.3 similarly shows a composition that stabilizes the biological activity of TNF. The method consists of combining TNF, also either in solid or liquid form, with a solution containing dissolved albumin. The resulting formulation of TNF is shown to be stable for only short periods of time when subjected to freezing, thawing, or lyophilization. Hereto, the problem associated with TNF oligmer formation is similarly not addressed. Moreover, it is important to point out that neither of these references present formulations that are free of particulate matter.

SUMMARY OF THE INVENTION

Accordingly, one aspect of the instant invention are TNF formulations suitable for parenteral administration that maintain the activity of TNF, in either liquid or solid form, for extended periods of time, and over a significant range of temperatures.

A second aspect of the invention are relatively temperature insensitive TNF formulations that retard or greatly reduce TNF oligomer formation, thereby imparting to such TNF formulations low immunogenicity and maintenance of biological activity.

A further aspect of the present invention are TNF formulations that have reduced particulate matter, and/or prevent the formation of particulate matter for prolonged periods of time over a significant range of temperatures while maintaining the biological activity of TNF.

An additional aspect of the invention is a TNF formulation that prevents the formation of oligomers that results from lyophilization, agitation or handling of the sample.

Another aspect of the instant invention are lyophilized TNF formulations having a low moisture content after prolonged storage at different temperatures and consisting of amorphous material, a polysaccharide, and a non-crystalizable physiologically acceptable buffer.

A further additional aspect of the invention is a liquid TNF formulation consisting of amorphous material, a polysaccharide and a phsysiologically acceptable buffer.

BRIEF DESCRIPTION OF THE DRAWINGS

Table I shows the compositions of 5 TNF formulations and the control formulation M/P.

Table II shows the bioactivity of the TNF formulations after storage at different temperatures for various times.

Table III compares the size of particulate matter present in the formulations, after the formulations were lyophilized and reconstituted with water.

Table IV presents light scattering data of lyophilized reconstituted formulations previously stored at different temperatures for 6 months prior to reconstitution.

Table V shows the percent TNF oligomers present in the formulations after they were stored lyophilized for different times and temperatures, and then reconstituted with water.

Table VI shows the percent moisture content of several formulations.

FIG. 3b shows the bioactivity of the TNF formulation S/M/C after reconstitution with water and storage at different temperatures for different times with or without shaking. Data for the control formulation, M/P, is also shown in FIG. 3a.

DETAILED DESCRIPTION OF THE INVENTION

Definitions

As referred to herein, tumor necrosis factor, or TNF, refers to a protein having the biological and physical properties commonly associated with this molecule in the scientific literature. Additionally, the term "recombinant" TNF refers to tumor necrosis factor produced by recombinant DNA techniques. Generally this consists of cloning the gene that codes for TNF by established recombinant DNA technology. By way of example, human TNF may be cloned by first obtaining a cDNA of the gene, and inserting the cDNA into a suitable vector. Numerous such vectors exist, and those most often employed are bacterial plasmids, particularly those that are compatible with the replicative functions of E. coli. The plasmid produced by the insertion of TNF cDNA is a recombinant plasmid that can be used to transform a suitable host cell. The cloned TNF gene can be expressed in the host cell, thereby producing recombinant TNF protein. The transformed host cell may be of either eucaryotic or procaryotic origin.

The definition of TNF, either the naturally occurring or recombinantly produced molecule, is further meant to encompass pharmaceutically acceptable forms of the molecule. For instance, TNF may be combined with pharmaceutically acceptable salts, or may be in neutral form. The free amino groups of the protein are, of course, capable of forming acid addition salts with, for example, in organic acids such as hydrochloric, phosphoric, or sulfuric acids; or, with organic acids such as, for example, acetic, glycolic, succinic, or mandelic acid. The free carboxyl groups on the molecule are also capable of forming salts with bases, including inorganic bases such as sodium, potassium, calcium hydroxides, and such organic bases as piperidine, glycocyamine, trimethylamine, choline, and caffeine. Further, other pharmaceutically acceptable forms of TNF can be realized by chemically modifying the molecule. Such modifications may occur by combining TNF with lipids and sacchardies, or by side chain modification such as acetylation of amino groups, phosphorylation of hydroxyl side chains, or oxidation of sulfhydryl groups. It will be appreciated by those skilled in the art that all these various pharmaceutically acceptable forms of TNF are meant to come within the scope of the definition of the molecule.

As referred to herein, the term "TNF mutein" is meant to encompass TNF molecules lacking 1-10 amino acids from the N-terminal sequence of the molecule. Additionally, the term is meant to encompass TNFs which lack or have reduced cysteine content. Examples of TNF muteins are referred to in U.S. Pat. No. 4,677,063 and U.S. Pat. No. 4,677,064. The disclosures of these patents are hereby incorporated by reference.

The term "pharmaceutically acceptable" refers to a carrier medium that does not negate or reduce the biological activity of formulated TNF, and that does not have any adverse biological effects when formulated TNF is administered to a patient.

As described herein, "crystallizing solute" is meant to encompass a substance which forms a crystalline matrix upon freezing below 0 degrees centigrade, and which does not display altered configuration upon freeze drying and subsequent elevation to room temperature.

The term, "stablizer" is meant to encompass a substance lacking crystalline structure at freezing temperatures.

Lastly, "organic hydrophilic polymer" is meant to encompass a macromolecule having a carbon-backbone with repeating monomer units with polar residues which render the polymer hydrophilic.

General Description

As mentioned above, TNF, which is the primary subject of the formulations described herein, may be naturally occurring TNF, obtainable from biological sources including cells, tissues, or organisms, or recombinant TNF, that is, TNF produced by DNA recombinant techniques. Naturally occurring TNF can be from any suitable species, such as, for example, mouse, rat, rabbit, pig, or human. Similarly, recombinant TNF can be derived from any number of species including mouse, rat, rabbit, pig and human. Preferably the TNF will be of human origin, and more preferably it will be human recombinant TNF. Typically, this molecule will be expressed in, and purified from a suitably transformed microorganism, preferably E. coli. However, other transformable cells, such as yeast and higher mammalian cells may also be employed.

The initial step in formulating TNF is to purify the molecule so that it is of sufficient pharmaceutical quality. Presently, there exist published purification schemes for TNF of either human or non-human origin. For example, the purification of rabbit TNF is described by Abele et al., FEB., 1985, Volume 180 (2), page 203. The purification of naturally occurring human TNF, or genetically engineered human TNF muteins are shown in U.S. Pat. Nos. 4,677,063 and 4,677,197, respectively. These publications are hereby incorporated by reference.

Briefly, the purification scheme for recombinant human TNF muteins most often consists of isolating TNF from bacterial cultures, or from extracts of bacterial cells wherein the TNF is sought to be purified away from contaminating bacterial proteins. The mixture is generally initially subjected to anion exchange chromatography which effectively binds the TNF, while not binding a considerable amount of the contaminants. The TNF can then be removed from the anion exchange column using a suitable salt gradient. A typical anion exchange chromatographic material is DEAE cellulose. Recombinant TNF elutes from this material when it is subjected to about 40 mM NaCl. Next, the TNF that has been eluted from the DEAE-cellulose column is brought to about 1.8 M-ammonium sulphate. Alternatively, the ionic strength of the solution can be adjusted with equivalent salts in the presence of 0.1M sodium phosphate buffer. This solution is subjected to hydrophobic chromatography, preferably chromatography employing a phenyl TSK support. The recombinant TNF binds to the hydrophobic chromatographic material and can be subsequently eluted by decreasing the concentration of ammonium sulphate, and finally the concentration of phosphate in the buffer. Next, fractions obtained from the hydrophobic chromatographic step containing TNF activity, as assayed by the methods shown in U.S. Pat. No. 4,677,063, are identified and subjected to filtration whereby recombinant TNF is separated from the salt remaining after the hydrophobic chromatographic step. A variety of gel filtration columns are available to accomplish this, such being, for example, G-200 and G-25 which are well known in the art, and manufactured by Pharmacia.

The TNF realized by the above purification method, as shown by sodium dodecyl sulfate poly-acrylamide gel electrophoresis (SDS-page), is homogeneous and suitable for formulation using the compositions of the instant invention.

A key feature of the TNF formulations described herein is that they retard or prevent the formation of TNF oligomers that arise as a result of lyophilization or handling of the sample. Additionally, the formulations lack significant particulate matter, and furthermore are agitation resistant in the sense that handling of the material does not result in the formation of particulate matter. It is important to note that the formation of oligomers is apparently independent of, and unrelated to the formation of particulate matter. Without intending to be bound to any particular theory, it appears that oligomer formation involves formation of multimers of TNF, whereas the particulate matter apparently results from a combination of organic and/or inorganic materials.

Formulations of TNF in accordance with this invention may be carried out as a separate operation using purified TNF, either naturally occurring or recombinant TNF, or in an operation that is integrated with the purification of either type of TNF as outlined above and described in the prior art. Most often, the formulation will consist of combining purified TNF with the formulation reagents. The instant formulations can be combined with TNF in either solid or liquid form. The preferred solid formulation is particularly usable with lyophilized TNF.

Both the lyophilized and liquid formulations have common reagents such as for, example, a stabilizer, organic hydrophilic polymer, and a physiologically acceptable buffer. One or more of each type of reagent may be present in a formulation. Since the definition of a suitable stabilizer is a substance that does not have a crystalline structure upon freezing below zero degrees centigrade, a partial list of stabilizers would include certain proteins, for example, human serum albumin, and oligosaccharides, such as, for example, sucrose, trehalose and lactose. Also, dextrans with molecular weights ranging from about 10,000 to 2,000,000 are suitable stabilizers. Additionally, certain organic hydrophilic polymers will also perform satisfactorily as the stabilizer component. By organic hydrophilic polymer is meant a macromolecule having a carbon backbone of repeating monomer units and having a substantially hydrophilic character due to the presence of polar residues, the latter being represented as functional groups associated with the backbone or as side chains. Non exclusive representative examples of organic hydrophilic polymers would include polyethylene glycol and polyvinylpyrrolidone, as well as other similar molecules well known to those skilled in the art.

In addition to the above, lyophilized formulations will also have a crystallizing solute. By the latter is meant a substance which forms a crystalline matrix upon freezing below zero degrees centigrade thereby producing a structure that maintains its integrity on lyophilization and subsequent exposure of the sample to elevated temperatures. Two nonexclusive examples of crystallizing solutes are mannitol and glycine. It will be appreciated by those skilled in the art that there are numerous other such crystallizing solutes which are essentially equivalent to these two.

Another property, of the lyophilized formulations is that they have a low moisture content when stored over a wide temperature range for long periods of time, such being, for example, $-20°$ C., $4°$ C., $25°$ C., and $37°$ C. for up to 6 months. Generally, the moisture content will be about 3.0%, (w/w) at the highest temperature, and 1.5% (w/w) or less at the lowest temperature. Moisture content is readily determined using standard coulometric techniques.

A general characteristic of liquid formulations is that they have a weight excess of the stabilizer component over TNF. Lyophilized formulations will also have a weight excess of stabilizer over TNF, but in addition, they will also have a crystallizing solute, and furthermore the crystallizing solute will be present in a weight ratio of at least 2 to 1 relative to the stabilizer material if the latter is an oligosaccharide.

Both the lyophilized and liquid formulations will have added to them a suitable physiologically acceptable buffer. Such might be citrate or phosphate buffers, or other buffers commonly employed to formulate pharmaceuticals for animal or human administration. However, phosphate is generally not preferred with oligogaccharides such as sucrose and trehalose but can be used with HSA, or dextran.

All of the formulations described herein maintain the bioactivity of TNF after the samples have been stored for about nine months over a broad range of temperatures. The bioactivity ranges from about $1-6 \times 10^7$ units.

Having described generally what the compositions of the lyophilized and liquid formulation are, several examples will be presented to further illustrate the range of formulations suitable for stabilizing TNF, as well as the properties attributable to these formulations. It will, of course, be understood by those skilled in the art that these examples are not intended to limit the invention in any manner.

It will be particularly appreciated by those skilled in the art that while the formulations described below have been exemplified as to the formulation of TNF that with suitable undue emperical manipulations and testing, these formulations may also be used to formulate other chemically similar cytokines. An example being colony stimulating factor-1.

EXAMPLE 1

Lyophilized Formulations

As referred to above, formulations suitable for maintaining TNF in lyophilized form, will consist of a suitable stabilizer such as a protein, polysaccharide, organic hydrophilic polymer, or oligosaccharide, and a physiological acceptable buffer, and a crystallizing solute.

Examples of the latter would include mannitol and glycine. Table I presents a description of 5 formulations that are particularly efficacious. Note that the abbreviations for the formulations are shown in parentheses at the end of each description. The first formulation, D/M/P, has the stabilizer dextran (D), the crystallizing solute mannitol (M), and sodium phosphate buffer (P). Dextran is present at about a 2 percent concentration, and mannitol at about a 1 percent concentration, and sodium phosphate buffer at a concentration of about 20 mM. The buffer is at a pH of about 7.4. Also, 0.25 milligrams/milliliter of TNF is present.

The second formulation, abbreviated D/M/C, is identical to D/M/P with the exception that the buffer is sodium citrate (C), and it is present at a concentration of about 10 mM, pH 6.5.

The third formulation, D/M/C+P, is identical to the second formulation with the exception that it contains sodium phosphate (+P), as well as sodium citrate buffer. Sodium phosphate is present at a concentration of about 2 mM. Additionally, the solution has a pH of about 7.0 and 0.25 mg/ml TNF.

The fourth formulation, abbreviated S/M/C, consists of 0.5% sucrose (S) and 1.5% mannitol (M). It also has 0.25 mg/ml TNF, and 10 mM sodium citrate (C), pH about 6.5.

The fifth formulation is identical to the third formulation with the exception that the stabilizer is 0.5% human serum albumin (H), and the solution has a pH of 6.5. This formulation is abbreviated H/M/C.

Also, note that Table I presents data for a control formulation, consisting of mannitol and phosphate which is abbreviated, M/P.

TABLE I

| | Description of Formulations | | |
| | Quantities, per ml. of Solution | | |
| Abbreviation | TNF | Buffer | Crystallizing Component | Stabilizer |
|---|---|---|---|---|
| M/P | 0.25 mg | 20 mM Phosphate pH 7.5 | 10 mg Mannitol | — |
| DMP | 0.25 mg | 20 mM Phosphate pH 7.4 | 10 mg Mannitol | 20 mg Dextran (79.4 K) |
| DMC | 0.25 mg | 10 mM Citrate pH 6.5 | 10 mg Mannitol | 20 mg Dextran (79.4 K) |
| DMCP | 0.25 mg | 10 mM Citrate + 2 mM Phosphate pH 7.0 | 10 mg Mannitol (79.4 K) | 20 mg Dextran |
| SMC | 0.25 mg | 10 mM Citrate pH 6.5 | 15 mg Mannitol | 5 mg Sucrose |
| HMC | 0.25 mg | 10 mM Citrate pH 6.5 | 10 mg Mannitol | 5 mg Human Serum Albumin |

EXAMPLE 2

Liquid Formulations

The same 5 formulations described above are also suitable for maintaining TNF in liquid form. The crystallizing solute, however, may be omitted without affecting the properties of the formulations.

EXAMPLE 3

Properties of Lyophilized Formulations

The instant lyophilized formulations have several appealling properties that will be described separately below. It will be noted, however, that these include reduced particulate matter arising from long term storage or agitation of the formulations, and reduced aggregation of TNF into oligomers. In addition, the formulations stabilize the bioactivity of TNF for extended periods of time, and have low moisture content and little protein heterogeneity. All of these properties are maintained over a significant temperature range.

Bioactivity of Lyophilized Formulations

Table II shows that all five lyophilized formulations maintain the bioactivity of TNF after storage at −20° C., 4° C., 25° C., 37° C. for about nine months. Moreover, even after storage at 47° C. for 14 days the formulations show little or no change in TNF activity. Bioactivity was determined by reconstituting the lyophilized samples with 1.2 ml of sterile distilled water, followed by assaying for TNF activity as described in U.S. Pat. Nos. 4,677,063 or 4,677,064.

TABLE II

| Bioactivity of Stability Samples: Specific Activity Expressed as $10^7$/U/mg | | | | | | | |
|---|---|---|---|---|---|---|---|
| Storage Temperature | Storage Time | Specific Activity[1] of | | | | | |
| | | M/P | DMP | DMC | DMCP | SMC | HMC |
| −20° C. | 14 days | — | 1.56 | 1.40 | 1.86 | 1.49 | 1.94 |
| | 42 days | — | 1.64 | 1.61 | 1.56 | 1.76 | 1.69 |
| | 91 days | — | 1.52 | 1.88 | 2.92 | 2.00 | 1.71 |
| | 150 days | — | 2.36 | 1.95 | 1.86 | 1.84 | 1.85 |
| | 179 days | — | 3.84 | 3.77 | 3.16 | 2.84 | 2.25 |
| | 273 days | — | 3.18 | 2.77 | 2.77 | 2.72 | 2.58 |
| 4° C. | 91 days | — | 1.61 | 6.66 | 3.66 | 4.13 | 2.27 |
| | 179 days | — | 5.43 | 3.55 | 3.73 | 2.81 | 2.81 |
| | 273 days | — | 2.73 | 2.79 | 2.49 | 2.58 | 2.74 |
| 25° C. | 91 days | 1.71 | 3.29 | 1.91 | 1.68 | 1.51 | 1.74 |
| | 179 days | 2.93 | 2.37 | 2.13 | 1.97 | 1.94 | 3.04 |
| | 273 days | 2.76 | 2.61 | 2.44 | 2.41 | 2.24 | 3.62 |
| 37° C. | 14 days | — | 1.40 | 1.44 | 1.22 | 1.61 | 1.23 |
| | 42 days | 1.31 | 1.65 | 1.63 | 1.45 | 1.50 | 1.81 |
| | 91 days | — | 1.41 | 1.50 | 1.42 | 1.84 | 1.93 |
| | 150 days | 1.82 | 1.76 | 2.05 | 1.64 | 2.10 | 2.15 |
| | 179 days | 2.54 | 2.20 | 2.07 | 1.74 | 2.09 | 2.53 |

TABLE II-continued

Bioactivity of Stability Samples:
Specific Activity Expressed as $10^7$/U/mg

| Storage Temperature | Storage Time | Specific Activity[1] of | | | | | |
|---|---|---|---|---|---|---|---|
| | | M/P | DMP | DMC | DMCP | SMC | HMC |
| | 273 days | 1.70 | 2.35 | 2.68 | 2.10 | 2.38 | 2.79 |
| 47° C. | 14 days | 1.14 | 1.09 | 1.28 | 1.51 | 1.26 | 1.80 |

[1]The values obtained fall within the normal variation of the assay.

Particulate matter a) Coulter Counter Assay

The number of particles per milliliter was measured in each of the five formulations described above. The measurements consisted of reconstituting the lyophilized formulations with 1.2 ml of sterile distilled water, followed by gently agitating the solution to disperse the reagents. Using a Coulter Counter machine, the number of particles of a pre-defined size was determined, and compared to the recommended number of particles for pharmaceutical preparations by the United States Pharmacopeia (USP) for drugs that are administered parenterally in small volumes. Particles present in the formulations above 3 sizes were assayed. Table III shows that particles above 6.84 um were present in all 5 formulations, with fewer particles being present in the formulation H/M/C. Particles larger that 9.87 um were also present in all the formulations. Formulations D/M/C+P, and H/M/C had the fewest particles above this size. Lastly, particles above 24.86 um were also determined, and, with the exception of the D/M/C and S/M/C formulations which had very few such particles, the remaining formulations exhibited no particles above this size. It is important to note that regardless of the size of the particles present in the various formulations, that the acceptable number of particles is well below that recommended by the USP, and these limits are shown at the bottom of the Table III.

TABLE III

Initial Values for Particulate Load in TNF Stability Samples

| Formulation | pH | Number of Particles/ml, Above | | |
|---|---|---|---|---|
| | | 6.84 μm | 9.87 μm | 24.86 μm |
| 1. Dex/Mann/Phos | 7.30 | 368 | 74 | 0 |
| 2. Dex/Mann/Cit | 6.60 | 570 | 110 | 2 |
| 3. Dex/Mann/C + P | 6.99 | 150 | 10 | 0 |
| 4. Suc/Mann/Cit | 6.60 | 142 | 44 | 2 |
| 5. HSA/Mann/Cit | 6.64 | 72 | 14 | 0 |
| Control - M/P | | 318 | 62 | 0 |
| U.S.P. | | 10,000 | 1,000 | | b) Light Scattering Assay

The light scattering properties of the various formulations were also determined. The procedure was similar to that described above wherein each sample was incubated at −20° C., 4° C., 25° C. and 37° C. centigrade for 6 months, and reconstituted with 1.2 ml of sterile distilled water. Measurements were taken immediately thereafter (0 hours), or at 4, 7 or 24 hours subsequent to reconstitution. Prior to a determination of the degree of light scattering of the 24 hour sample, it was manually and vigorously shaken for 10 seconds.

Table IV shows the light scattering data obtained when the amount of scattering at 90 degrees is determined with a standard fluorimeter. None of the samples exhibit a scattering number of 500 or greater even after shaking. For comparative purposes it is important to note that a solution having a scattering number of 500 is generally clear.

TABLE IV

Light Scattering by Reconstituted Lyophilized Formulations of TNF[1]

| Formulation | Storage Conditions | Light Scattering After Reconstituted Solution Held at 4° C. For | | | |
|---|---|---|---|---|---|
| | | 0 Hrs. | 4 Hrs. | 7 Hrs. | 24 Hrs. (+ Shaken) |
| DMP | 6 months at −20° C. | 112 | 111 | 107 | 483 |
| | 6 months at 4° C. | 131 | 126 | 132 | 355 |
| DMC | 6 months at −20° C. | 92 | 96 | 102 | 544 |
| | 6 months at 4° C. | 124 | 119 | 116 | 470 |
| DMCP | 6 months at −20° C. | 99 | 89 | 94 | 406 |
| | | 111 | 109 | 108 | 325 |
| SMC | 6 months at −20° C. | 17 | 10 | 11 | 342 |
| | 6 months at 4° C. | 18 | 16 | 16 | 448 |
| HMC | 6 months at −20° C. | 255 | 262 | 256 | 519 |
| | 6 months at 4° C. | 261 | 260 | 265 | 542 |

Oligomers

Four of the five exemplary formulations described above were also tested for the presence of oligomers after the lyophilized formulations had been stored at different temperatures for various times, and reconstituted with 1.2 mls of sterile distilled water. The percent oligomers in the formulations was determined by electrophoresing the formulations using sodium dodecyl sulfate polyacrylamide gel electrophoresis, and scanning the gels with a densitometer. The percent oligomers was calculated by measuring the area attributed to the oligomers and dividing by the total area resulting from non-aggregated and aggregated TNF and multiplying by 100. It is apparent from Table V that when the formulations are stored at minus 20° C. for up to nine months, with the possible exception of S/M/C, oligomers are not detectable in any of the formulations.

After storage for about 3 months at 2°–8° C., the formulations D/M/P, D/M/C+P and S/M/C, exhibit oligomers, whereas D/M/C does not. Curiously, when the formulations were stored for 6 or 9 months, none of the formulations exhibited oligomers. Formulations stored at 25° C. for about 3, 6 or 9 months exhibit few or no oligomers. Similar results were observed when the formulations were stored at 37° C. or 47° C. It will be noted that there are apparent inconsistent results in the percent oligomers present in formulations stored at 2°–8° C. For instance, D/M/P, D/M/C+P and S/M/C when stored for 3 months but not 6 or 9 months exhibits oligomers. Most likely this is due to technical difficulties in measuring small amounts of oligomer.

For comparative purposes, Table V shows the percent oligomers in a formulation lacking a stablizer and consisting of 0.25 mg/ml TNF, 1% Mannitol, and 20 mM phosphate buffer, pH 7.5. It is apparent that this formulation exhibits significant oligomers when stored at either 25° C., 37° C., or 47° C.

Lastly, oligomers were measured in the H/M/C formulation by Western blot analysis wherein TNF is visualized using TMB an anti-TNF monoclonal antibody followed by addition of horse radish peroxidase goat anti-mouse polyclonal antibody, and then the substrate. These procedures are well known to those skilled in the art, and mouse anti-TNF monoclonal antibodies are readily available. This procedure was necessary because of the high concentration of human serum in the sample which precluded accurate densitometric determinations. In any event, it was determined that the H/M/C formulation lacked detectable oligomers after storage at either 25° C. or 37° C. for about 9 months.

TABLE V

Oligomer Formation in TNF Stability Samples

| Storage Temperature | Storage Time | Percent Oligomers in Formulation | | | | |
|---|---|---|---|---|---|---|
| | | M/P | DMP | DMC | DMCP | SMC |
| −20° C. | 7 days | 0.00 | 0.00 | 0.00 | 0.00 | 0.00 |
| | 14 days | 0.00 | 0.00 | 0.00 | 0.00 | 0.00 |
| | 42 days | 0.00 | 0.00 | 0.00 | 0.00 | 0.00 |
| | 91 days | 0.00 | 0.00 | 0.00 | 0.00 | 0.00 |
| | 150 days | 0.00 | 0.00 | 0.00 | 0.00 | 0.51 |
| | 179 days | 0.00 | 0.00 | 0.00 | 0.00 | 0.00 |
| 2–8° C. | 91 days | 0.00 | 1.40 | 0.00 | 0.30 | 0.70 |
| | 179 days | 0.00 | 0.00 | 0.00 | 0.00 | 0.00 |
| | 273 days | 0.00 | 0.00 | 0.00 | 0.00 | |
| 25° C. | 91 days | 0.80 | 0.48 | 0.50 | 0.51 | 0.78 |
| | 179 days | 2.00 | 0.26 | 0.26 | 0.00 | 0.79 |
| | 273 days | 1.80 | 0.07 | 0.00 | 0.00 | 0.00 |
| 37° C. | 14 days | 0.00 | 0.00 | 0.00 | 0.00 | 0.00 |
| | 42 days | 2.42 | 0.37 | 0.19 | 0.47 | 0.00 |
| | 91 days | 4.53 | 1.63 | 0.57 | 0.91 | 0.16 |
| | 150 days | 4.25 | 0.63 | 0.54 | 0.66 | 0.00 |
| | 179 days | 7.70 | 2.30 | 0.00 | 0.00 | 0.20 |
| | 273 days | 11.40 | 0.93 | 0.88 | 0.47 | 0.48 |
| 47° C. | 7 days | 1.93 | 0.35 | 0.20 | 0.38 | 0.00 |
| | 14 days | 1.34 | 0.00 | 0.43 | 0.31 | 0.52 |

Moisture Content

The instant formulations wre developed to have low moisture content after prolonged storage at different temperatures because moisture present in the lyophilized formulations adversely effects the the long term stability of TNF. The moisture content of the formulations was determined using a Karl Fischer Coulometry. Table VI presents the results obtained from samples stored for 6 months at either −20° C., 4° C., 25° C., and 37° C. The results for three formulations are shown in the Table. It is apparent that the moisture content at −20° C. and 4° C. is very similar, whereas at 25° C. and 37° C. it is approximately double that of the lower temperatures. At the lowest temperature there is about 1.5% (w/w) moisture present, whereas there is about 3% (w/w) at the highest temperature.

TABLE VI

Moisture Uptake by Experimental Formulations

| Formulation | % Moisture in Formulation After Storage for Six Months at | | | |
|---|---|---|---|---|
| | −20° C. | 4° C. | 25° C. | 37° C. |
| M/P | 2.65 | 2.93 | 2.09 | 1.46 |
| M/P | — | — | 3.23 | 2.54 |
| DMG | 0.99 | — | — | 2.97 |
| SMC | 1.34 | 1.69 | 3.03 | 2.78 |
| HMC | 0.79 | — | — | 3.33 |

Heterogeneity

Figure 1:
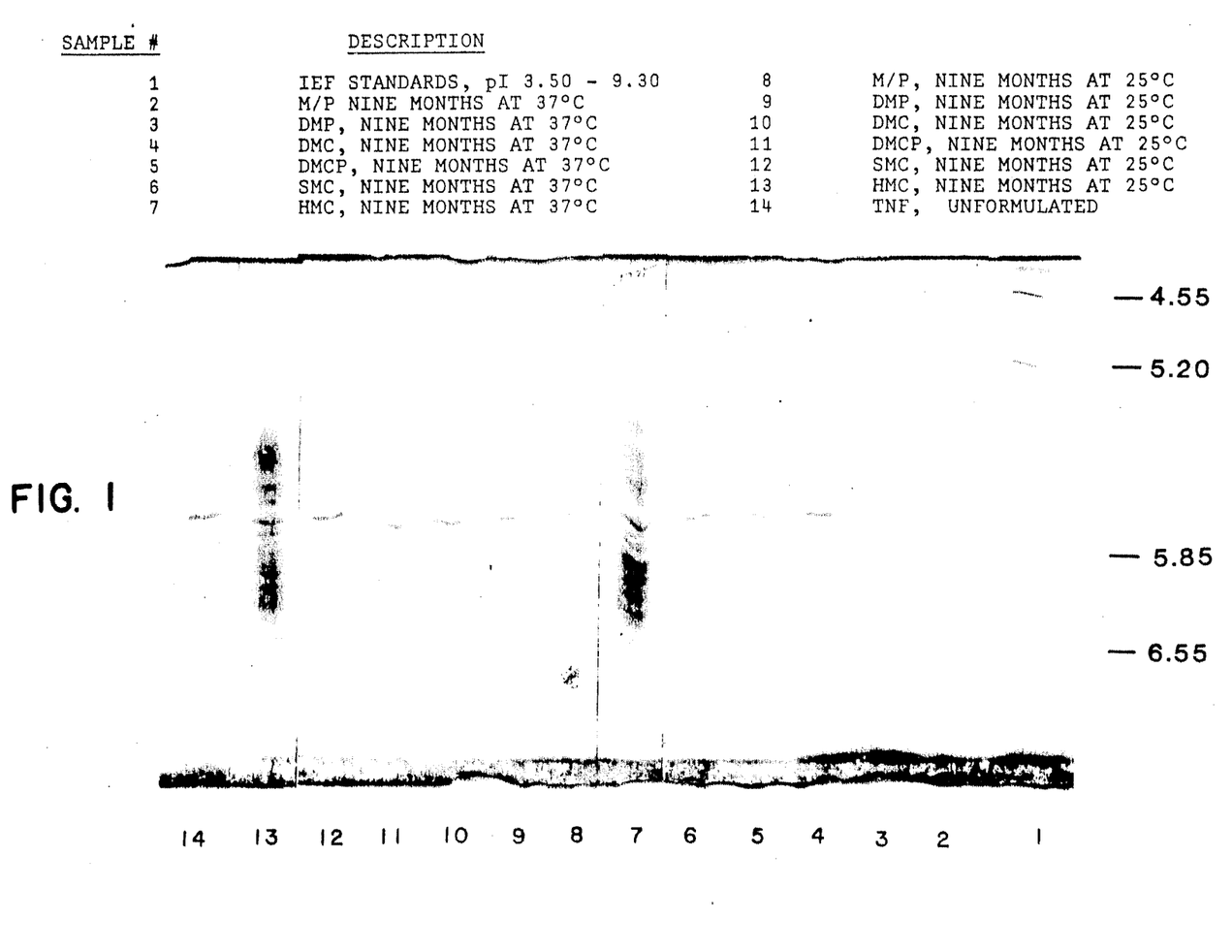
FIG. 1 shows the isoelectric focusing profiles of the TNF formulations.

FIG. I shows the isoelectric focusing profiles for several of the lyophilized formulations after the samples were stored at either 2°–8° C., 25° C. or 37° C. for 9 months prior to reconstitution and focusing. Generally, focusing was conducted using standard conditions and reagents well known to those skilled in the art at a pH of about 4–6.5, and at a voltage of 1500 and amperage of 50 milliamps. The focusing patterns were compared to the control, mannitol, phosphate, formulation referred to above, which exhibits a significant heteroenous pattern when the sample is stored at 37° C. for 9 months. In consrast, the D/M/C+P, S/M/C D/M/P, D/M/P, and H/M/C formulations revealed little or no variation in the isoelectric profiles when the samples were stored for 9 months at the various temperatures studied.

Stability of Reconstituted Solutions and Effect of Agitators

Figure 2A:
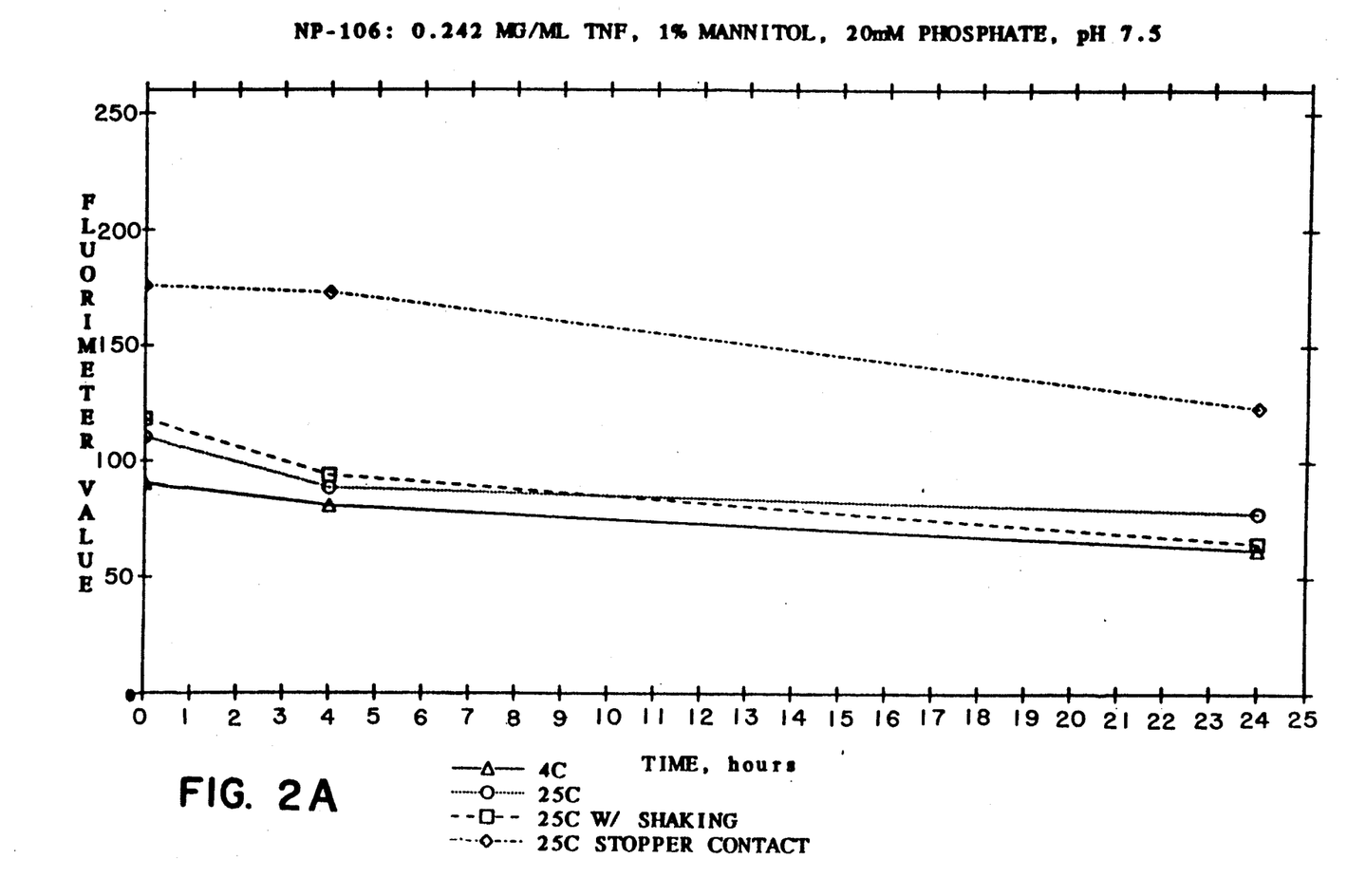
FIG. 2a and 2b present the bioactivity of TNF in the M/P and S/M/C formulations, respectively, after lyophilization at different temperatures for up to nine months.
Figure 2B:
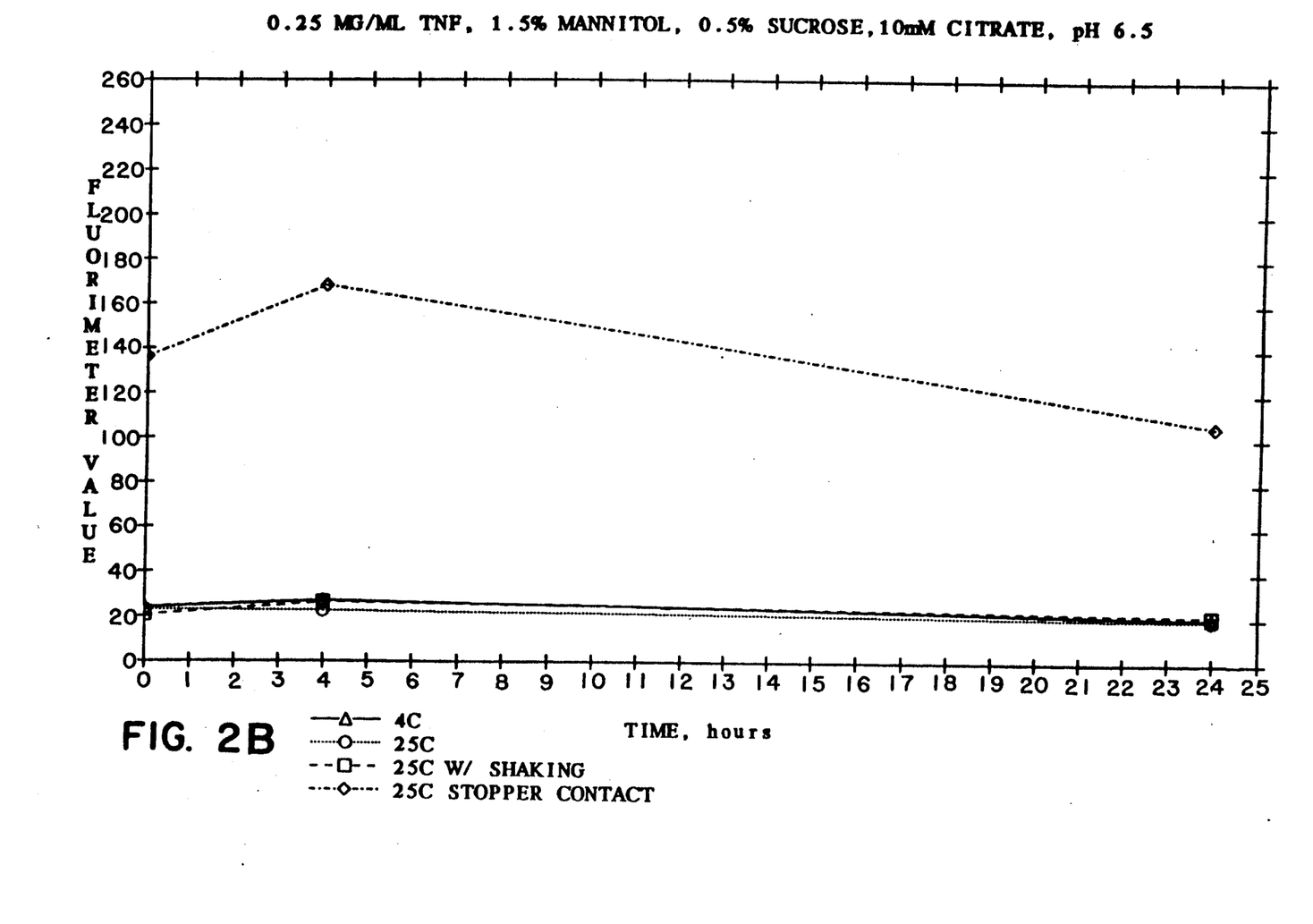

Studies were carried out to determine the short-term stability of the TNF formulations after reconstitution. Several experiments were done to determine the particulate content, and the bioactivity of the formulations. The samples were reconstituted, and then held at either 4° C. or 25° C. for either 4 or 24 hours. For all five formulations shown in Table I light scattering experiments revealed no change in the amount of particulate matter present in the solution at either temperature and at either time period. FIG. 2 shows the results for the S/M/C formulation. Moreover, if the sample was shaken thereby causing the formulation to contact the sides of the glass container, but not touch the top of the stopper, and then stored at 25° C. for 4 or 24 hours there was also no increase in particulate matter. However, if the solution was shaken and the formulation allowed to contact the stopper (13 mm gray butyl West) there was a small but detectable increase in light scattering suggesting particle formation arising as a result of the dissolution of small particles associated with the stopper (FIG. 2). However, although these particles are detectable by light scattering they are not apparent to the naked eye.

Figure 3A:
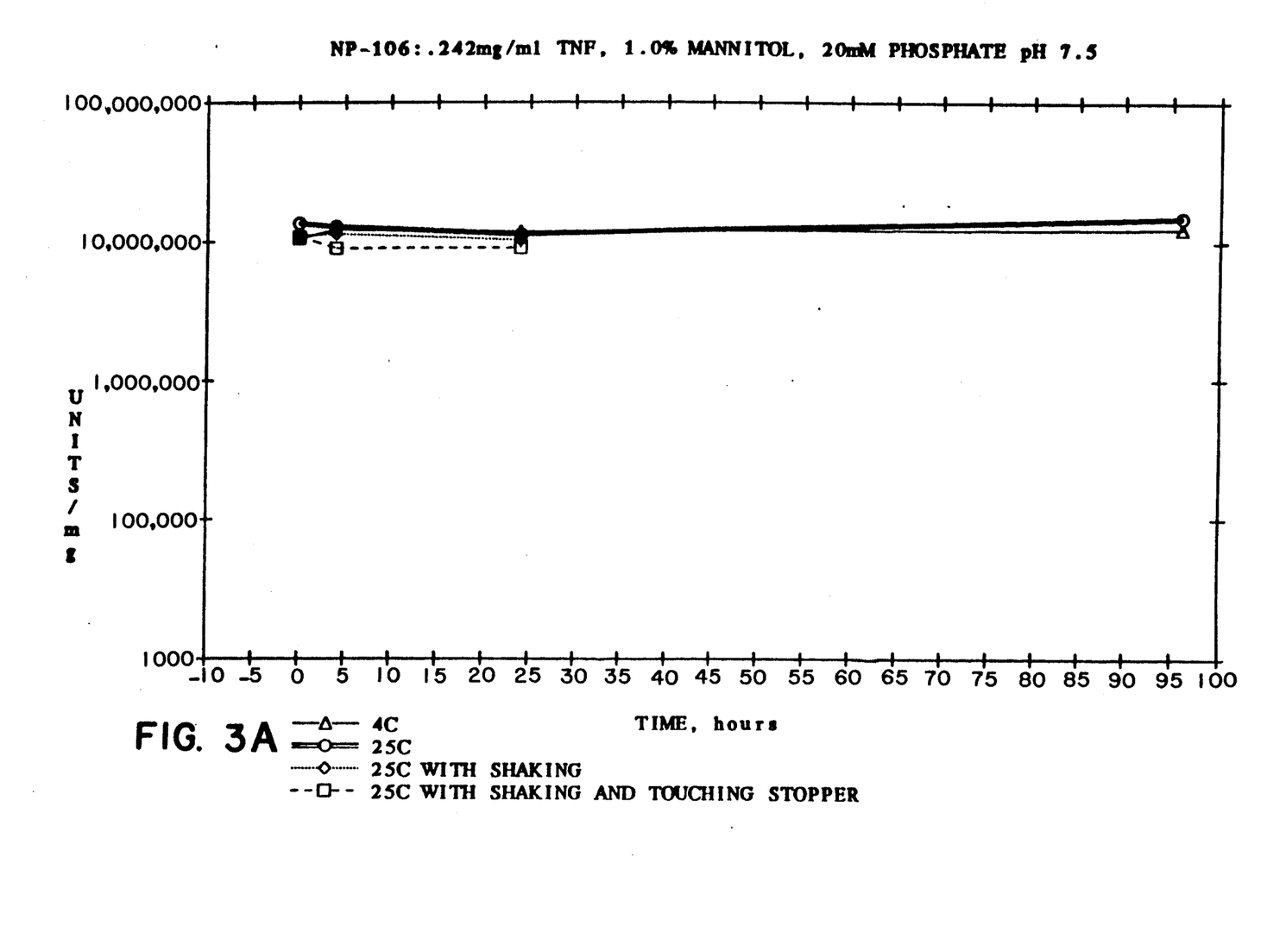
Figure 3B:
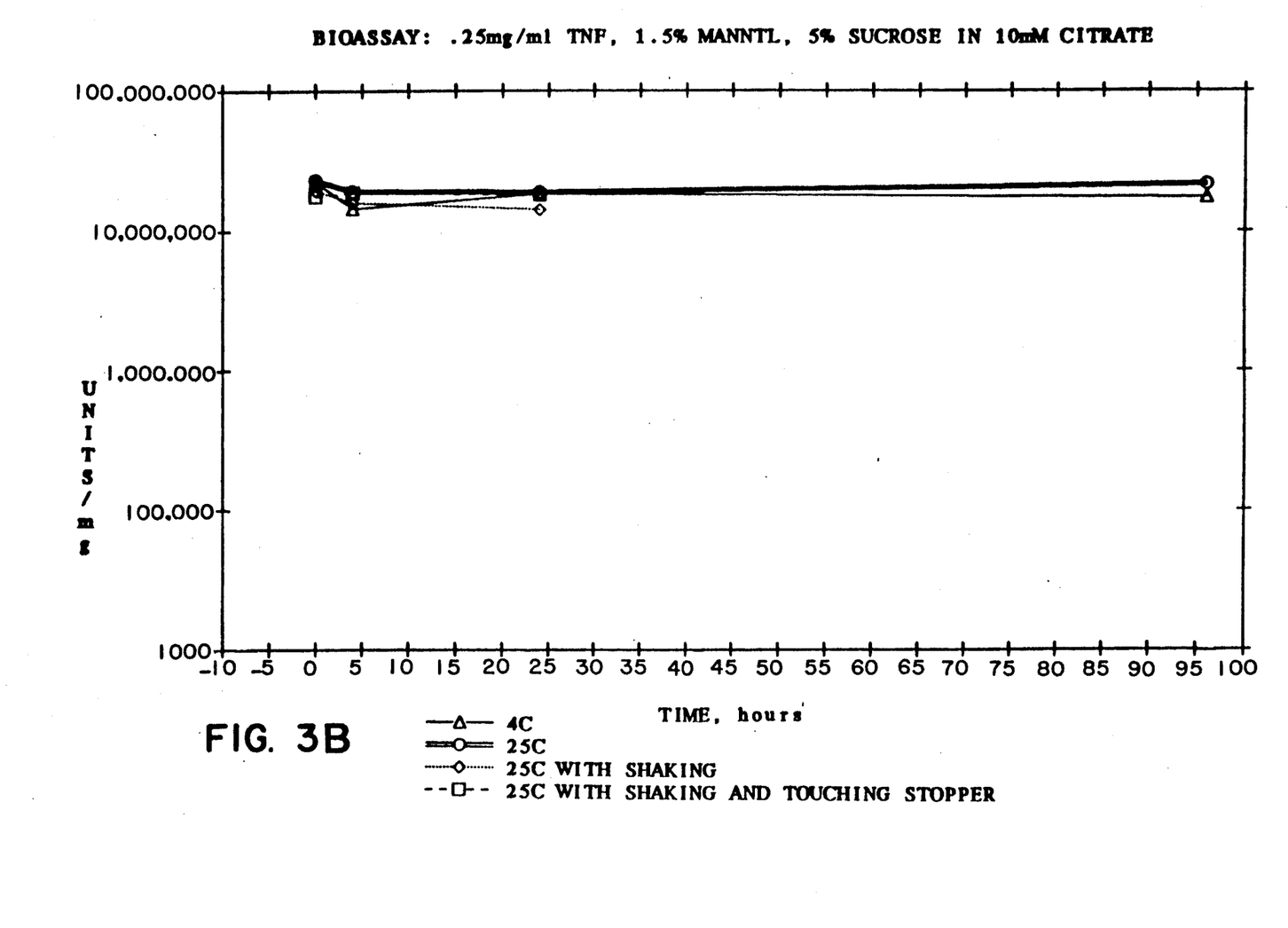

The bioactivity of the five reconstituted formulations shown in Table I when kept at for 25° C. 4 or 24 hours is not diminished. This is true regardless if the formulation is shaken, and either does or does not contact the stopper. Moreover, the bioactivity of S/M/C is maintained if the solution is stored at 25° C. for up to 96 hours, and this is shown in FIG. 3 along with the results for the control formulations M/P.

It will, of course, be appreciated by those skilled in the art that there are numerous modifications and substitutions that are possible and regularly employable in the instant invention. These alternative modes for carrying out the invention are intended to be within the scope of the invention, the invention being limited solely by the scope of the following claims.

What is claimed is:

1. A pharmaceutical preparation for parenteral administration to a patient to provide tumor necrosis factor (TNF) therapy thereto comprising a mixture of 1) a therapeutically effective amount of TNF, 2) a weight excess over the TNF of a physiologically acceptable stabilizer material that does not affect the stability of the TNF adversely wherein said stabilizer material is selected from the group consisting of human serum albumin, dextran, polyethylene glycol, polysorbate 80, polyvinylpyrrolidone, sucrose, lactose, or trehalose, 3) a physiologically acceptable buffer, said buffer being selected from the group consisting of citrate, phosphate, or citrate-phosphate, and 4) an effective amount of a physiologically acceptable crystallizing solute, provided that if the stabilizer material is an oligosaccharide, said crystallizing solute is present in a weight ratio with the solute of at least 2:1 to 3:1, and is selected from the group consisting of mannitol or glycine.

2. The preparation of claim 1 comprising the following reagents in approximate amounts; 0.25 mg/ml TNF, 10 mM phosphate buffer, 10 mg/ml mannitol, and 20 mg/ml dextran.

3. The preparation of claim 1 comprising the following reagents in approximate amounts; 0.25 mg/ml TNF, 10 mM citrate buffer, 10 mg/ml mannitol, and 20 mg/ml dextran.

4. The preparation of claim 1 comprising the following reagents in approximate amounts; 0.25 mg/ml TNF, 10 mM citrate buffer, 2 mM phosphate buffer 15 mg/ml mannitol, and 20 mg/ml dextran.

5. The preparation of claim 1 wherein said stabilizer material is sucrose or human serum albumin.

6. The preparation of claim 1 comprising the following reagents in approximate amounts; 0.25 mg/ml TNF, 10 mM citrate buffer, 15 mg/ml mannitol, and 5 mg/ml sucrose.

7. The preparation of claim 1 comprising the following reagents in approximate amounts; 0.25 mg/ml TNF, 10 mM citrate buffer, 10 mg/ml mannitol, and 20 mg/ml human serum albumin.

8. The preparation of claim 1 comprising the following reagents in approximate amounts; 0.25 mg/ml TNF, 10 mm citrate buffer, 1.4% sucrose and 4.2% mannitol.

9. The preparation of claim 1 comprising the following reagents in approximate amounts; 0.5 mg/ml TNF, 10 mm citrate buffer, 0.5% sucrose, and 1.5% mannitol.

10. The preparation of claim 6, said preparation having not more than about 44 9.87 $\mu$m particles per milliliter nor more than about 2 24.86 $\mu$m particles per milliliter.

11. The preparation of claim 7, said preparation having not more than about 13 9.87 $\mu$m particles per milliliter and particles not greater than about 24.86 $\mu$m.

12. A liquid pharmaceutical preparation having less than about 2% tumor necrosis factor (TNF) oligomer for parenteral administration to a patient to provide TNF therapy thereto comprising 1) a therapeutically effective amount of TNF, 2) a weight excess over the TNF of a physiologically acceptable stabilizer material wherein said stabilizer material is selected from the group consisting of human serum albumin, dextran, polyvinylpyrrolidone, polysorbate 80, lactose, sucrose, or trehalose, and 3) a physiologically acceptable noncrystallizable buffer said buffer being selected from the group consisting of citrate, phosphate, and citrate-phosphate.

13. A liquid pharmaceutical preparation having less than about 2% tumor necrosis factor (TNF) oligomer suitable for parenteral administration to a patient to provide TNF therapy thereto comprising 1) a therapeutically effective amount of TNF, 2) a weight excess over the TNF of a physiologically acceptable stabilizer material selected from the group consisting of sucrose or human serum albumin, and 3) a physiologically acceptable noncrystallizable buffer comprising citrate.

* * * * *